(12) United States Patent
Lei et al.

(10) Patent No.: US 8,099,158 B2
(45) Date of Patent: Jan. 17, 2012

(54) SYSTEM AND METHOD FOR SELECTING END OF DIASTOLE AND END OF SYSTOLE FRAMES

(75) Inventors: Weng Lei, Mount Prospect, IL (US); John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1173 days.

(21) Appl. No.: 11/848,505

(22) Filed: Aug. 31, 2007

(65) Prior Publication Data

US 2008/0281218 A1 Nov. 13, 2008

Related U.S. Application Data

(60) Provisional application No. 60/916,329, filed on May 7, 2007.

(51) Int. Cl.
*A61B 5/04* (2006.01)
(52) U.S. Cl. .................................................... 600/523
(58) Field of Classification Search .................. 600/523, 600/508, 407, 410, 450; 345/418
See application file for complete search history.

(56) References Cited

U.S. PATENT DOCUMENTS

| | | | |
|---|---|---|---|
| 5,533,085 A * | 7/1996 | Sheehan et al. | 378/95 |
| 6,368,285 B1 * | 4/2002 | Osadchy et al. | 600/508 |
| 6,438,403 B1 * | 8/2002 | Cline et al. | 600/410 |
| 2007/0236491 A1 * | 10/2007 | Hundley et al. | 345/418 |

OTHER PUBLICATIONS http://en.wikipedia.org/wiki/Electrocardiogram.
http://www.cals.ncsu.edu/physiology/images/wiggers.gif.
Hemodynamics is a 12-Letter Word! An intro to the basics. Part I: Basics with Wiggers. Mar. 2007. Jon E. Jenkins.

* cited by examiner

*Primary Examiner* — George Manuel
*Assistant Examiner* — Robert Wieland
(74) *Attorney, Agent, or Firm* — Alexander J Burke

(57) ABSTRACT

A method and apparatus for automatically selecting an end of diastole image frame and an end of systole image frame for cardiac analysis. In the method and apparatus, a plurality of image frames of a heart having a contrast medium injected into the heart and an electrocardiogram (ECG) curve of the heart are obtained. Candidate image frames are identified in the plurality of image frames that correspond to a first predetermined point on the ECG curve of the heart associated with the end of diastole. An end of diastole image frame is selected from the candidate image frames. An end of systole image frame is then identified and selected from the remaining one of the plurality of image frames.

23 Claims, 5 Drawing Sheets

SYSTEM AND METHOD FOR SELECTING END OF DIASTOLE AND END OF SYSTOLE FRAMES

RELATED APPLICATIONS

This application claims the benefit of U.S. Provisional Application Ser. No. 60/916,329 filed on May 7, 2007, the entire disclosure of which is incorporated herein by reference.

FIELD

An embodiment of the invention relates to cardiac analysis. More particularly, an embodiment of the invention relates to a system and method for automatically selecting an end of diastole image frame and an end of systole image frame for cardiac analysis.

BACKGROUND

The heart contracts and relaxes with each heartbeat cycle. During contraction (systole), the heart ejects blood from two pumping chambers called ventricles. During relaxation (diastole), the ventricles of the heart refill with blood.

Not all of the blood is emptied from the ventricles of the heart during contraction or systole. End of systole (ES) refers to the volume of blood remaining in the ventricles immediately after systole and before the beginning of ventricular relaxation or diastole whereas ejection fraction refers to the percentage of blood which is pumped out of a filled ventricle during systole. End of diastole (ED) refers to the volume of blood remaining in the ventricles at the end of filling, i.e., when the ventricles refill with blood.

Some cardiac procedures involve a Left Ventricle Analysis (LVA) to analyze the ejection fraction, ED volume, ES volume, and other operating parameters of the heart. The analysis focuses on the left ventricle because it is the heart's main pumping element.

The LVA may be performed using angiography. To perform LVA using angiography, a user (e.g., cardiologist) must manually inspect every x-ray image frame of the angiography series in order to find the frames depicting ED and ES so that the ED and ES volumes can be ascertained. As may be expected, the manual inspection of every x-ray image frame of the angiography series is time consuming.

Accordingly, there is need for a system and method that reduces the time required to find ED and ES frames in an angiography series.

SUMMARY

A method is disclosed for automatically selecting an end of diastole image frame and an end of systole image frame for cardiac analysis. The method comprises the steps of obtaining a plurality of image frames of a heart having a contrast medium injected therein; obtaining an electrocardiogram (ECG) curve of the heart while performing the image frames obtaining step; identifying candidate image frames in the plurality of image frames that correspond to a first predetermined point on the ECG curve of the heart, the first predetermined point on the ECG curve associated with the end of diastole; selecting from the candidate image frames an image frame that shows the greatest amount of the contrast medium injected into the heart, the selected image frame comprising the end of diastole image frame; and identifying and selecting from the remaining one of the plurality of image frames an image frame that corresponds to a second predetermined point on the ECG curve of the heart and the selected end of diastole image frame, the second predetermined point on the ECG curve associated with the end of systole and the identified and selected image frame comprising the end of systole image frame.

Also disclosed is a system for automatically selecting an end of diastole image frame and an end of systole image frame for cardiac analysis. The system comprises a first sub-system for obtaining a plurality of image frames of a heart having a contrast medium injected into the heart; a second sub-system for obtaining an electrocardiogram (ECG) curve of the heart; and a processing unit in communication with the first and second sub-systems. The processing unit identifies candidate image frames in the plurality of image frames that correspond to a first predetermined point on the ECG curve of the heart, the first predetermined point on the ECG curve associated with the end of diastole; selects from the candidate image frames an image frame that shows the greatest amount of the contrast medium injected into the heart, the selected image frame comprising the end of diastole image frame; and identifies and selects from the remaining one of the plurality of image frames an image frame that corresponds to a second predetermined point on the ECG curve of the heart and the selected end of diastole image frame, the second predetermined point on the ECG curve associated with the end of systole and the identified and selected image frame comprising the end of systole image frame.

DETAILED DESCRIPTION

A system and method is described herein for automatically finding ED x-ray image frames and ES x-ray image frames in a plurality of x-ray image frames of an angiography series, and selecting from the found ED and ES x-ray image frames the ED and ES x-ray image frames which show the greatest amount of contrast medium injected into the heart and preferably into the left ventricle of the heart. The system and method may be integrated into a quantitative analysis application to automatically select ED and ES x-ray image frame candidates for doctors when performing Left Ventricle Analysis.

Figure 1:
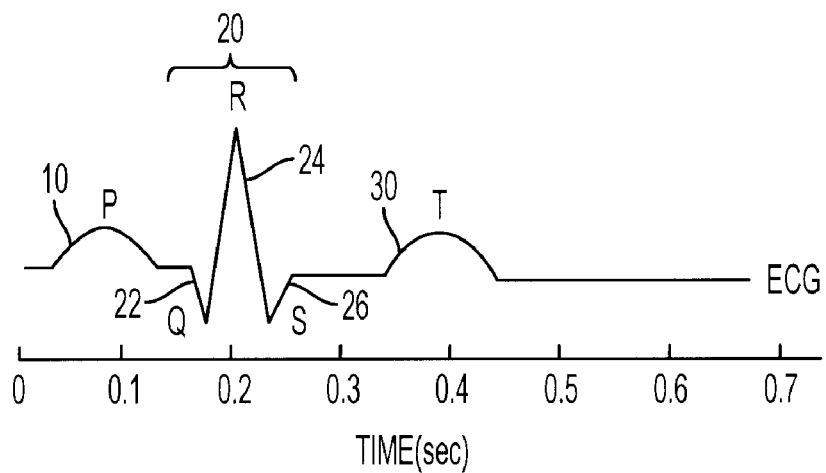
FIG. 1 is a diagram of an ECG waveform of a normal heartbeat.

The system and method uses electrocardiogram (ECG) data corresponding to the x-ray image frames of the angiography series to automatically find the ED and ES x-ray image frames in the plurality of x-ray image frames of the angiography series and presents them to a user. As is well known, an electrocardiogram (ECG) graphically records the electrical activity of the heart over time in the form of an ECG tracing or waveform or tracing. FIG. 1 shows an ECG waveform of a normal heartbeat. As shown, the ECG waveform includes a P wave 10; a QRS complex 20 formed by a Q wave 22 an R wave 24 and an S-wave 26; and a T wave 30. These waves represent the depolarization and repolarization of the atria and ventricles of the heart.

The P wave 10 of the ECG represents the depolarization that spreads from the sinoatrial SA node throughout the atria. The QRS complex 20 of the ECG represents the depolarization of the ventricles. The T wave 30 represents the repolarization of the ventricles (atria repolarization occurs during ventricle depolarization but the wave is not visible in the ECG waveform because its amplitude is small and masked by the QRS complex).

Figure 2:
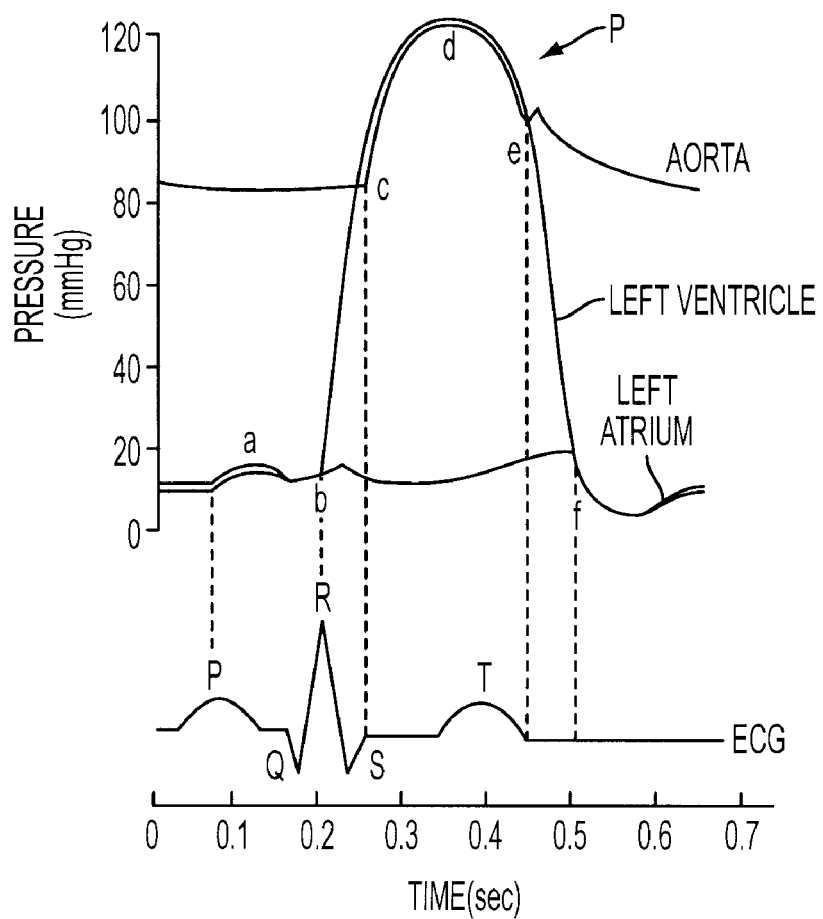
FIG. 2 is a Wiggers Diagram.

FIG. 2 shows a well known Wiggers Diagram, which includes an ECG at the bottom of the diagram that illustrates a normal heartbeat and a pressure curve P at the top of the diagram that illustrates the corresponding pressure changes in the atria, ventricles and aorta. The Wiggers Diagram is used herein to help illustrate how ED and ES x-ray image frames are selected in accordance with the principles of the invention.

Referring still to FIG. 2, the time between points "a" and "b" on pressure curve P represents the blood filling phase of the heart. The time between points "b" and "c" on pressure curve P represents a period during which all the heart valves are closed and isometric contraction of the heart occurs. The isometric contraction period is essential because the ventricles must generate enough pressure to open the aortic valve and deliver blood to the body. The time between points "c" and "e" on pressure curve P is known as the systolic ejection phase. The systolic ejection phase is the period of time when the heart muscle is contracting with great force to eject blood from the ventricles. Between points "e" and "f" is the isovolumetric relaxation phase. During this period, all valves are closed. Blood is not traveling anywhere. The ventricle is relaxing and decreasing in pressure. At point "f", the mitral valve between the atrium and ventricle is open. The left ventricle enters the filling phase again. The next diastole-systole cycle will have similar waveforms as illustrated in the diagram.

Figure 3:
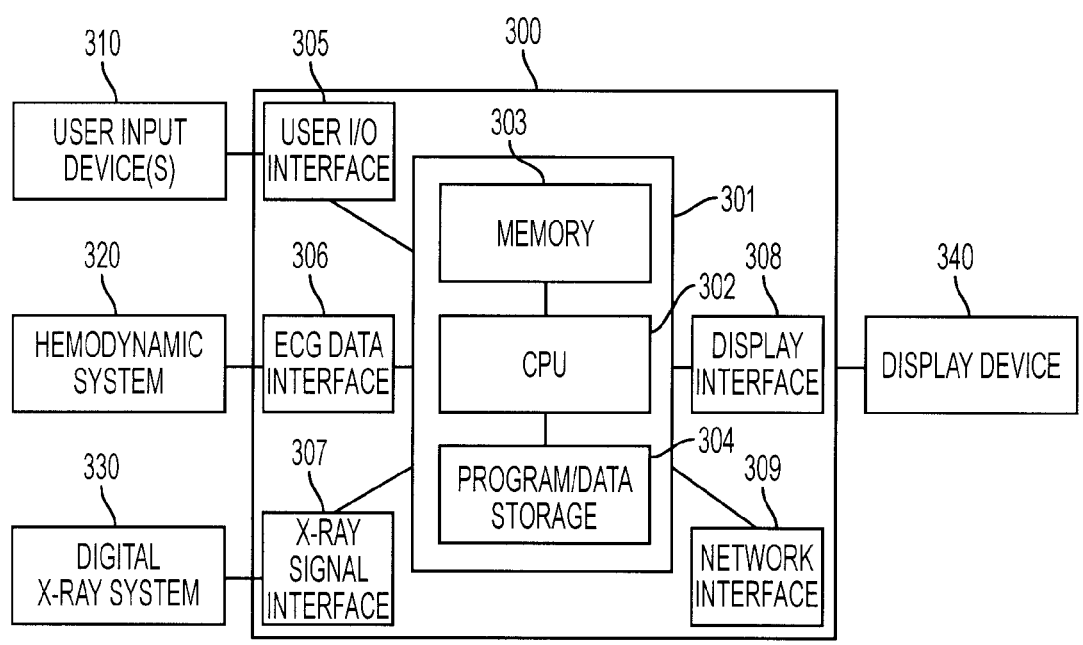
FIG. 3 is a block diagram of an exemplary embodiment of the system for automatically finding ED x-ray image frames and ES x-ray image frames.

FIG. 3 shows a block diagram of an exemplary embodiment of the system for automatically finding ED x-ray image frames and ES x-ray image frames. The system comprises a computer system 300 including a computer 301 in data communication with a user input/output (I/O) interface 305, an ECG data interface 306, an x-ray signal interface 307, a display interface 308 and a network interface 309. The system further comprises external peripheral devices and sub-systems including one or more user input devices 310, a hemodynamics sub-system 320, a digital x-ray sub-system 330, and a display device 340.

The computer 301 includes a central processing unit (CPU) 302 in communication with a memory 303 and a program/data storage unit 304. The program/data storage unit 304 provides long-term storage of programs and data associated with the methods described herein while the memory 303 provides temporary storage of programs and data associated with the methods describe herein. The CPU 302 executes the programs (e.g., algorithms) associated with the methods describe herein which are stored in the program/data storage unit 304 and memory 303.

The one or more user input devices 310, in one exemplary embodiment, includes a keyboard and mouse (neither shown) for generating digital user input data for controlling and operating the system. In other embodiments, the one or more user input devices 310 may include trackballs, pen lights (neither shown) and any other suitable user input device or combination of devices. The digital user input data generated by one or more user input devices 310 is supplied to the computer 301 via the user I/O interface 301.

The hemodynamics sub-system 320 may include conventional and unconventional means for obtaining digital ECG and blood pressure data (aortic, ventricular and atrial pressure data) of the patient's heart. Such means may include invasive and/or non-invasive devices for obtaining digital ECG and blood pressure data of the patient's heart. The digital ECG and blood pressure data generated by the hemodynamics sub-system 320 is supplied to the computer 301 via the ECG data interface 306.

The digital x-ray sub-system 330 may include conventional and unconventional means for generating the angiography series comprising the plurality of digital x-ray images frames of the patients heart and digital x-ray image data corresponding to the angiography series. The digital x-ray image data generated by the x-ray sub-system 330 is supplied to the computer 301 via the x-ray signal interface 307.

The user I/O, ECG data, x-ray signal, display and network interfaces 305, 306, 307, 308, 309 may be conventional or unconventional in design and operation. The display device 340 may be a conventional or unconventional monitor or display screen for displaying images and data.

The computer 310 processes and analyzes the digital ECG, blood pressure and x-ray image data in accordance with the methods described herein to select best ED and ES x-ray image frame candidates. The selected ED and ES x-ray image frame candidates are displayed by the system on the display device 340 for acceptance or rejection by the user.

The network interface 309 allows data corresponding to the selected ED and ES x-ray image frames to be communicated to another computer, a database, and the like over a computer network including, without limitation, a wide area network or local-area network.

Figure 4:
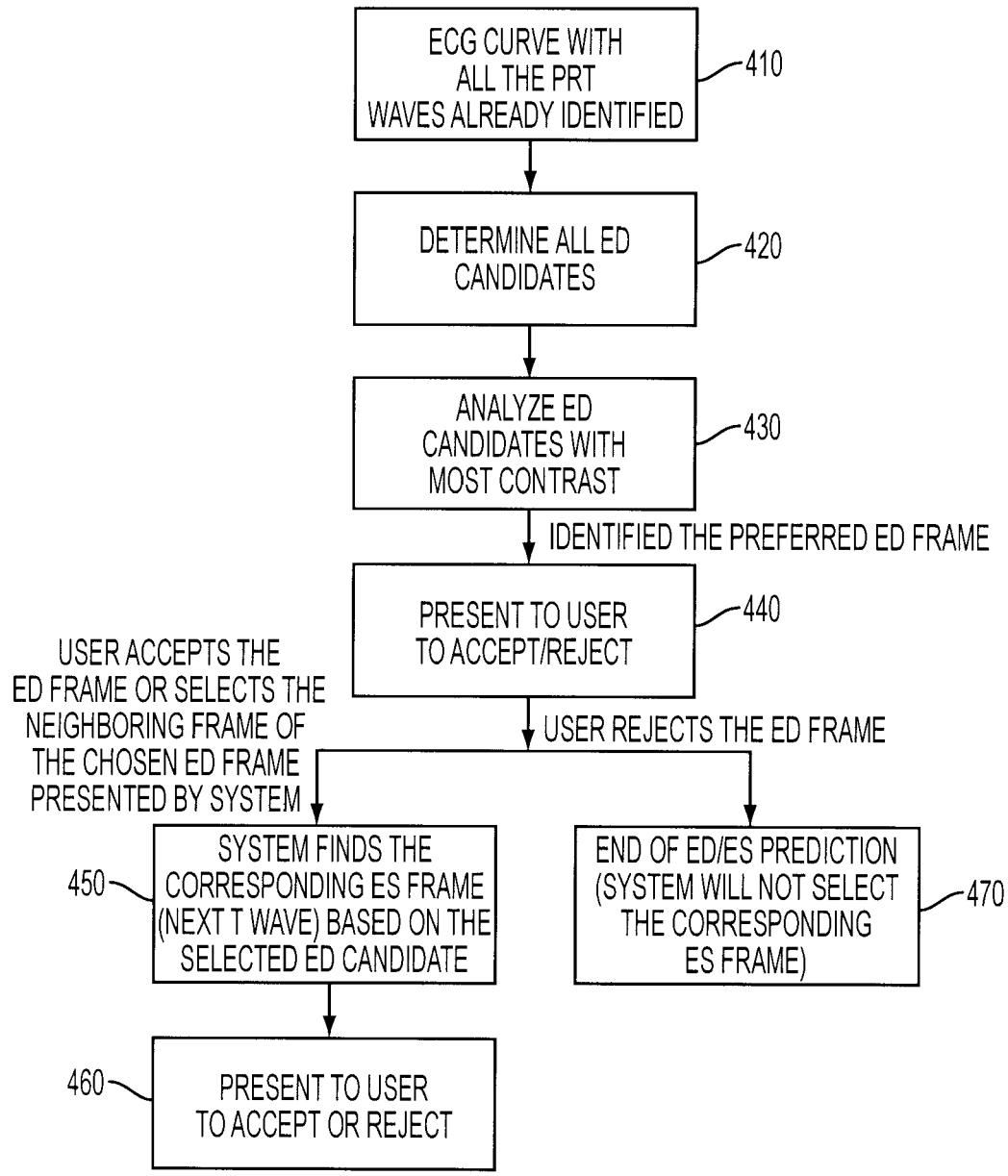
FIG. 4 is a flowchart of a method for automatically finding ED x-ray image frames and ES x-ray image frames according to an exemplary embodiment.

FIG. 4 is a flowchart outlining the steps of a method for automatically finding ED x-ray image frames and ES x-ray image frames according to an exemplary embodiment. The method will be described in the context of the system described above and shown in FIG. 3. One of ordinary skill in the art will of course appreciate that the method may be performed using other suitable system.

Referring now to FIGS. 3 and 4, the method commences in step 410 wherein a ECG curve of a patient's heart is obtained using the hemodynamics system 320. At the same time the ECG curve is obtained, a plurality of x-ray image frames of the heart are obtained by the digital x-ray system 330. Each of the x-ray image frames corresponds to a certain portion of the ECG curve. The plurality of x-ray image frames of the heart are obtained after the patient's heart (e.g. the left ventricle) has been injected with a contrast medium. The data representing the ECG curve and the x-ray image frames are transmitted to the computer 301 of the computer system 300 via the ECG data interface 306 and the x-ray signal interface 307, respectively. To make the analysis of the ECG curve less prone to high-frequency noise, the ECG curve may be filtered, in one exemplary embodiment, with a low-pass filter to eliminate frequencies above 30 Hz. In any case, the transmitted data may be stored in the memory 303 of the computer 301.

Figure 8:
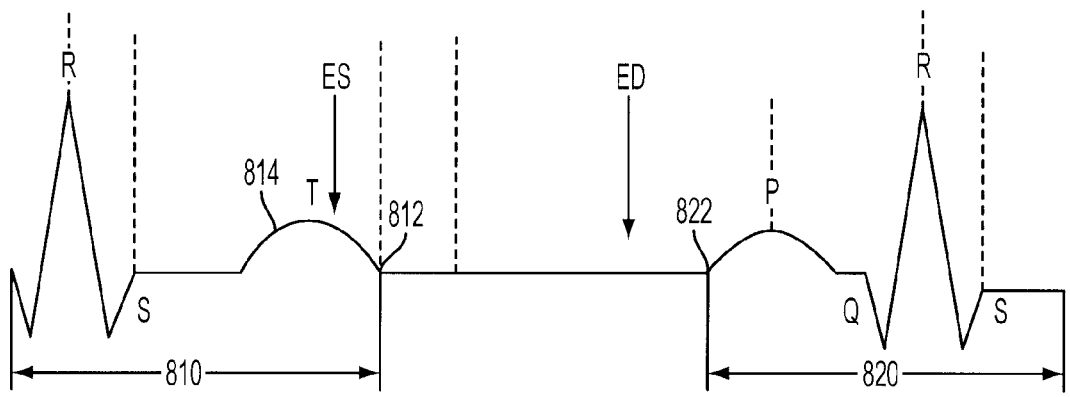
FIG. 8 is a diagram of an ECG curve comprising two ECG waveforms.

In step 420 of the method, candidate ED x-ray image frames are identified by the computer 301 in the plurality of x-ray image frames. More specifically, the CPU 302 executes a ECG/frame mapping algorithm stored in the program/data storage unit 304 using the ECG curve and x-ray image frame data stored in the memory 303, as shown in the functional block diagram of FIG. 5. The mapping algorithm temporally matches the ECG curve waveform portions, i.e., P waves, Q waves, R waves, S waves, and T waves, to their corresponding x-ray image frames 0, 1, 2, 3, 4, 5, . . . in block 510. For example, x-ray image frame 1 shows an image of the heart as it generates a P wave in a certain ECG waveform (EGC cycle or period), x-ray image frame 2 shows an image of the heart as it generates an R wave in that ECG waveform, and x-ray image frame 4 shows an image of the heart as it generates a T wave in that ECG waveform. The algorithm determines or identifies in block 520 candidate ED x-ray image frames 530 that correspond to predetermined points on the ECG curve of the patient's heart that are most likely to be associated with or linked to the end of diastole. Each of the candidate ED x-ray image frames 530 corresponds with one of the predetermined points of a corresponding one of the ECG waveforms contained within the acquired ECG curve. In a preferred embodiment, as shown in FIG. 8, each of the predetermined points on the ECG curve that are most likely to be associated with or linked to the end of diastole comprises point ED, which is about 70% of the distance between the falling edge 812 of the T wave in corresponding ECG waveform 810 and the leading edge 822 of the P wave of the ECG waveform 820 which immediately follows ECG waveform 810.

Figure 5:
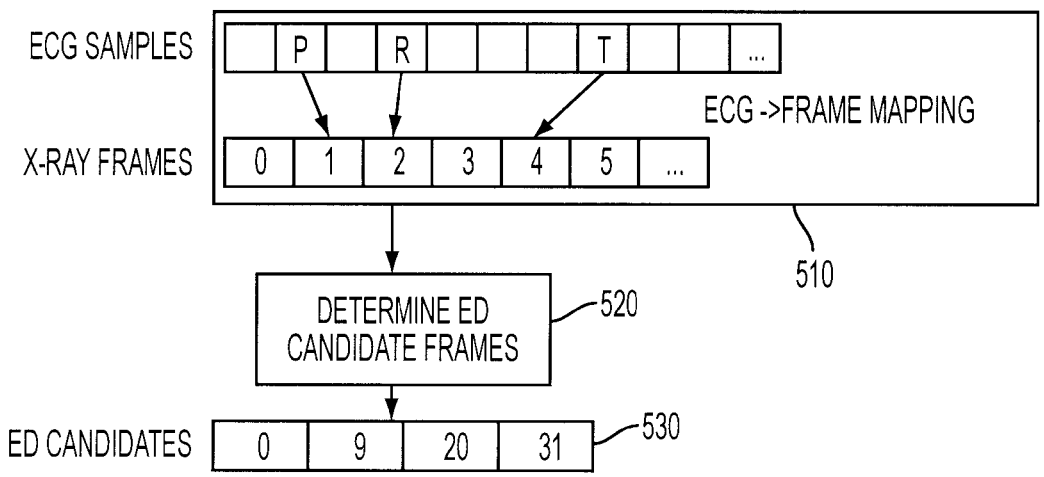
FIG. 5 is a functional block diagram of an exemplary process for determining ED candidate x-ray image frames.

Using the examples shown in FIG. 5, the computer 301 determines that x-ray image frames 0, 9, 20, and 31 each shows an image of the patient's heart as it generates the electrical activity corresponding to the predetermined point ED of the ECG curve, or in other words, each shows an image of the patient's heart at the end of diastole. Thus, x-ray image frames 0, 9, 20, and 31 qualify as candidate ED x-ray image frames.

Figure 6:
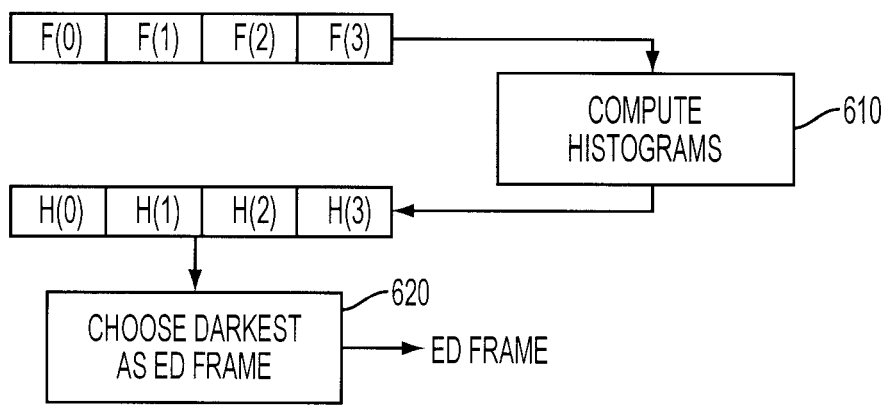
FIG. 6 is a functional block diagram of an exemplary process for selecting an ED x-ray image frame from the ED candidate x-ray image frames.

In step 430 of the method, the computer 301 selects the best ED x-ray image frame from the group of ED x-ray image frame candidates, using the process shown in the functional block diagram of FIG. 6. In block 610 of FIG. 6, the CPU 302 executes any suitable histogram algorithm stored in the program/data storage unit 304 of the computer 301 using candidate x-ray image frame data stored in the memory 303 and calculates a histogram for each candidate ED x-ray image frame.

In block 620 of FIG. 6, the computer 301 selects the best ED x-ray image frame from the group of ED x-ray image frame candidates by analyzing the histograms to determine which candidate ED x-ray image frame has the most pixels in the darkest approximately 25% of the histogram. More specifically, the CPU 302 executes an algorithm stored in the program/data storage unit 304 of the computer 301 which compares the histograms to determine which candidate ED x-ray image frame has the most pixels in the darkest approximately 25% of the histogram. Such algorithms are well known in the art and may used for this purpose in this process. The ED x-ray image frame that is determined to have the most pixels in the darkest approximately 25% of the histogram, i.e., the ED x-ray image frame that shows the greatest amount of the contrast medium injected into the heart, is selected by the computer 301 as the ED x-ray image frame.

In step 440 of the method, the selected ED x-ray image frame is presented to the user on the display device 340 of the system. If the user accepts the selected ED x-ray image frame, the computer 301 selects a corresponding ES x-ray image frame based on the selected ED x-ray image frame in step 450. If the user does not accept the selected ED x-ray image frame but instead selects a neighboring frame of the selected ED x-ray image frame, the computer 301 selects a corresponding ES x-ray image frame based on the selected ED x-ray image frame in step 450, as will be explained further on.

If the user does not accept the selected ED x-ray image frame, step 470 of the method ends the process and no corresponding ES x-ray image frame is selected.

Figure 7:
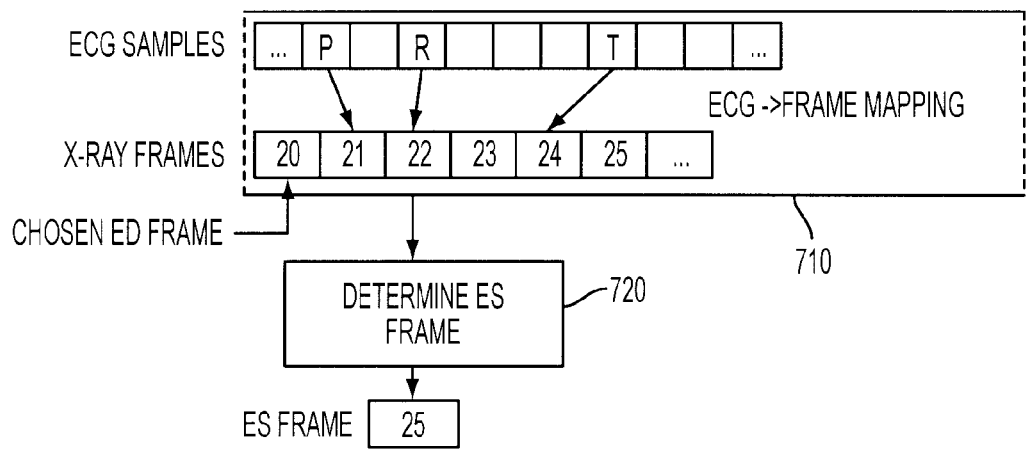
FIG. 7 is a functional block diagram of an exemplary process for selecting an ES x-ray image frame corresponding to the selected ED x-ray image frame.

The computer 301 selects the ES x-ray image frame from the plurality of x-ray image frames based on the corresponding selected ED x-ray image frame in step 450 by executing the ECG/frame mapping algorithm stored in the program/data storage unit 304 with the CPU 302 using the ECG curve and x-ray image frame data stored in the memory 303, as shown in the functional block diagram of FIG. 7. The mapping algorithm temporally matches the ECG curve waveform portions, i.e., P waves, Q waves, R waves, S waves, and T waves, to their corresponding x-ray image frames 20, 21, 22, 23, 24, 25, . . . in block 710. For example, x-ray image frame 21 shows an image of the heart as it generates a P wave in a certain ECG waveform, x-ray image frame 22 shows an image of the heart as it generates an R wave in that ECG waveform, and x-ray image frame 24 shows an image of the heart as it generates a T wave in that ECG waveform. The algorithm determines or identifies in block 720 the x-ray image frame that corresponds to the selected ED x-ray image frame and that corresponds to a predetermined point on the ECG curve of the patient's heart that is most likely to be associated with or linked to the end of systole. In a preferred embodiment, as shown in FIG. 8, the predetermined point on the ECG curve that is most likely to be associated with or linked to the end of systole comprises a point ES that is about 30% of the distance starting at the maximum amplitude 814 of the T wave of the ECG waveform 810 (wherein the maximum amplitude is either positive as shown or negative in the case of an inverted T wave) and ending at the falling edge 812 of the T wave of the waveform 810.

Using the examples shown in FIG. 7, the computer 301 takes the selected ED x-ray image frame 20 and selects corresponding ES x-ray image frame 25 which shows an image of the patient's heart as it generates the electrical activity that corresponds to the predetermined point ES of the ECG curve, or in other words, shows an image of the patient's heart at the end of systole.

In step 460 of the method, the selected ES x-ray image frame is presented to the user on the display device 340 of the system for acceptance or rejection.

Aspects of the present invention may be embodied in other specific forms without departing from the spirit or essential attributes of the disclosure. Accordingly, reference should be made to the appended claims, rather than the foregoing specification, as indicating the embodiments of the invention. Although the foregoing description is directed to exemplary embodiments, it is noted that other variations and modification will be apparent to those skilled in the art, and may be made without departing from the spirit or scope of the invention.

What is claimed is:

1. A method for automatically selecting an end of diastole image frame and an end of systole image frame for cardiac analysis, the method comprising the steps of:
   obtaining a plurality of image frames of a heart having a contrast medium injected therein;
   obtaining an electrocardiogram (ECG) curve of the heart while performing the image frames obtaining step;
   identifying candidate image frames in the plurality of image frames that correspond to a first predetermined point on the ECG curve of the heart between predetermined different ECG heart cycle wave segments, the first predetermined point on the ECG curve being associated with the end of diastole;

selecting from the candidate image frames an image frame that shows the greatest amount of the contrast medium injected into the heart, the selected image frame comprising the end of diastole image frame; and identifying and selecting from the remaining image frames of the plurality of image frames an image frame that corresponds to the selected end of diastole image frame and a second predetermined point on the ECG curve of the heart within at least one predetermined ECG heart cycle wave segment, the second predetermined point on the ECG curve being associated with the end of systole and the identified and selected image frame comprising the end of systole image frame.

2. The method according to claim 1, wherein the ECG curve includes a T wave and a P wave following the T wave, the first predetermined point on the ECG curve comprising about 70% of a distance starting at a falling edge of the T wave and ending at a leading edge of the P wave.

3. The method according to claim 2, wherein the second predetermined point on the ECG curve comprises about 30% of a distance starting at a maximum amplitude of the T wave and ending at a falling edge of the T wave.

4. The method according to claim 1, wherein the ECG curve includes a T wave, the second predetermined point on the ECG curve comprises about 30% of a distance starting at a maximum amplitude of the T wave and ending at a falling edge of the T wave.

5. The method according to claim 1, wherein the selected end of systole image frame follows the selected end of diastole image frame.

6. The method according to claim 1, wherein the plurality of image frames comprise x-ray image frames.

7. The method according to claim 1, wherein the image frames obtaining step is performed by angiography.

8. The method according to claim 1, displaying the selected end of diastole and systole image frames.

9. The method according to claim 1, further comprising the step of transmitting the selected end of diastole and systole image frames over a network.

10. The method according to claim 1, wherein the step of selecting from the candidate image frames the image frame that shows the greatest amount of the contrast medium injected into the heart is performed by generating a histogram of each of the candidate image frames and comparing the histograms to one another.

11. A system for automatically selecting an end of diastole image frame and an end of systole image frame for cardiac analysis, the system comprising:

a first sub-system for obtaining a plurality of image frames of a heart having a contrast medium injected therein;

a second sub-system for obtaining an electrocardiogram (ECG) curve of the heart; and a processing unit in communication with the first and second sub-systems, the processing unit for:

identifying candidate image frames in the plurality of image frames that correspond to a first predetermined point on the ECG curve of the heart between predetermined different ECG heart cycle wave segments, the first predetermined point on the ECG curve being associated with the end of diastole;

selecting from the candidate image frames an image frame that shows the greatest amount of the contrast medium injected into the heart, the selected image frame comprising the end of diastole image frame; and identifying and selecting from the remaining image frames of the plurality of image frames an image frame that corresponds to the selected end of diastole image frame and a second predetermined point on the ECG curve of the heart within at least one predetermined ECG heart cycle wave segment, the second predetermined point on the ECG curve being associated with the end of systole and the identified and selected image frame comprising the end of systole image frame.

12. The system according to claim 11, wherein the ECG curve includes a T wave and a P wave following the T wave, the first predetermined point on the ECG curve comprising about 70% of a distance starting at a falling edge of the T wave and ending at a leading edge of the P wave.

13. The system according to claim 12, wherein the second predetermined point on the ECG curve comprises about 30% of a distance starting at a maximum amplitude of the T wave and ending at a falling edge of the T wave.

14. The system according to claim 11, wherein the ECG curve includes a T wave, the second predetermined point on the ECG curve comprises about 30% of a distance starting at a maximum amplitude of the T wave and ending at a falling edge of the T wave.

15. The system according to claim 11, wherein the selected end of systole image frame follows the selected end of diastole image frame.

16. The system according to claim 11, wherein the plurality of image frames comprise x-ray image frames.

17. The system according to claim 11, wherein the image frames are obtained by angiography.

18. The system according to claim 11, wherein the first sub-system comprises an x-ray sub-system.

19. The system according to claim 11, wherein the first sub-system comprises a digital x-ray sub-system.

20. The system according to claim 11, wherein the second sub-system comprises a hemodynamics sub-system.

21. The system according to claim 11, further comprising a display device for displaying the selected end of diastole and systole image frames.

22. The system according to claim 11, further comprising a network interface for transmitting the selected end of diastole and systole image frames over a network.

23. The system according to claim 11, wherein selecting from the candidate image frames the image frame that shows the greatest amount of the contrast medium injected into the heart includes generating a histogram of each of the candidate image frames and comparing the histograms to one another.

* * * * *